United States Patent [19]
Mallet et al.

[11] Patent Number: 5,654,143
[45] Date of Patent: Aug. 5, 1997

[54] RNA AMPLIFICATION METHOD REQUIRING ONLY ONE MANIPULATION STEP

[75] Inventors: François Mallet, Villeurbanne; Guy Oriol, Saint-Chamond; Bernard Mandrand, Villeurbanne, all of France

[73] Assignee: Bio Merieux, Marcy L'Etoile, France

[21] Appl. No.: 412,229

[22] Filed: Mar. 27, 1995

Related U.S. Application Data

[63] Continuation of Ser. No. 53,498, Apr. 29, 1993, abandoned.

[30] Foreign Application Priority Data

Apr. 29, 1992 [FR] France .................. 92 05322

[51] Int. Cl.$^6$ .................. C12Q 1/68; C12P 19/34
[52] U.S. Cl. .................. 435/6; 435/91.2
[58] Field of Search .................. 435/5, 6, 91.1, 435/91.2, 91.21; 935/77, 78

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 5,021,335 | 6/1991 | Tecott et al. . |
| 5,229,297 | 7/1993 | Schnipelsky et al. .......... 436/94 |

FOREIGN PATENT DOCUMENTS

| | | |
|---|---|---|
| 0397463 | 11/1990 | European Pat. Off. . |
| 0479158 | 4/1992 | European Pat. Off. . |
| 2669347 | 5/1992 | France . |
| 8601827 | 3/1986 | WIPO . |
| 9102817 | 7/1991 | WIPO . |
| 9109944 | 7/1991 | WIPO . |

OTHER PUBLICATIONS

W. T. Tse et al., "Reverse Transcription and Direct Amplification of Cellular RNA Transcripts by Taq Polymerase", *Gene*, vol. 88, No. 2, Apr. 16, 1990, pp. 293–296.

E. Shimomaye et al., "Use of Avian Myeloblastosis Virus Reverse Transcriptase at High Temperature for Sequence Analysis of Highly Structured RNA", *Gene Analysis Techniques*, vol. 6, No. 2, Mar./Apr. 1989, pp. 25–28.

Goblet, C., "One-Step Amplification of Transcripts in Total RNA Using the Polymerase Chain Reaction", *Nucleic Acids Research*, vol. 17, No. 5, (1989) p. 2144.

Schwartz, S. et al., "Cloning and Functional Analysis of Muliply Spliced mRNA Species of Human Immunodeficiency Virus Type I", *Journal of Virology*, vol. 64, No. 6, Jun. 1990, pp. 2519–2529.

Nuovo, G., et al. "Detection of Human Papillomavirus DNA in Formalin–fixed Tissues by *In Situ* Hybridization After Amplification by Polymerase Chain Reaction", *Am. J. Pathol.*, 139, 847–854 (1991).

Becker–Andre, M. et al., Absolute mRNA Quantification Using the Polymerase Chain Reaction (PCR). A Novel Approach by a PCR Aided Transcript Titration Assay (PATTY) *Nucleic Acids Res.*, (17):9437–9447 (1989).

Chirgwin, J.M. et al., "Isolation of Biologically Active Ribonucleic Acid from Sources Enriched in Ribonuclease", *Biochem.*, 18: 5294–5299 (1979).

Gilsin, V., et al. "Ribonucleic Acid Isolated by Cesium Chloride Centrifugation", *Biochem.*, 13:2633–2638 (1973).

Myers, T.W., et al. "Reverse Transcription and DNA Amplification by a *Thermus Thermophilus* DNA Polymerase", *Biochem.*, 30:7661–7666 (1991).

Robert–Guroff, M. et al., "Structure and Expression of tat–, rev–, and nef–Specific Transcripts of Human Immunodeficiency Virus Type 1 in Infected Lymphocytes and Macrophages", *J. Virol.*, 64 (7):3391–3398 (1990).

Guatelli, J.C., et al., "Alternative Splice Acceptor Utilization during Human Immunodeficiency Virus Type 1 Infection of Cultured Cells", *J. Virol.*, 64 (9):4093–4098 (1990).

Benko, D.M. et al., "A Novel Human Immunodeficiency Virus Type 1 Protein, tev, Shares Sequences with tat, env, and rev Proteins", *J. Virol.*, 64:2505–2518 (1990).

Schwartz, S., et al., "Env and Vpu Proteins of Human Immunodeficiency Virus Type I Are Produced from Multiple Bicistronic mRNAs", *J. Virol.*, 64 (11):5448–5456 (1990b).

Holland, S.M. et al., "Immunodefiency Virus Rev Protein Recognizes a Target Sequence in Rev–Responsive Element RNA within the Context of RNA Secondary Structure", *J. Virol.*, 64 (12):5966–5975 (1990b).

Lawrence, J. et al. *Human Retroviruses and Aids*, (1990), edited by Myers, G., et al.

*Primary Examiner*—Eggerton A. Campbell
*Attorney, Agent, or Firm*—Oliff & Berridge

[57] ABSTRACT

An RNA amplification method is particularly useful for diagnosing bacterial or viral infections or genetic disorders and for cell typing. The method includes the steps of denaturing a solution containing RNA, synthesizing a first cDNA strand from a suitable primer in the presence of reverse transcriptase, denaturing the heteroduplex formed, synthesizing a second cDNA strand from a second primer in the presence of DNA polymerase and then subjecting the cDNA formed to a sufficient number of amplification cycles. All the reactants and solvents are first placed in the same container to provide a single manipulation step that avoids the risk of contamination.

18 Claims, 11 Drawing Sheets

RNA AMPLIFICATION METHOD REQUIRING ONLY ONE MANIPULATION STEP

This is a continuation of application Ser. No. 08/053,498 filed Apr. 29, 1993, now abandoned.

The invention relates to a method for the amplification of ribonucleic acid (RNA), in which all the ingredients needed for the various reactions are introduced into the starting solution, all the steps being performed in the same container and without subsequent addition of any ingredient. It is thus possible to work in a closed container throughout the duration of the operations, and hence to reduce the risks of accidental contamination and the risk of manipulation error.

BACKGROUND OF THE INVENTION

The ability now exists to amplify a DNA sequence without it being necessary to clone it in a host cell. The best known technique in this field is the so-called polymerase chain amplification technique, often designated by the acronym PCR, described, for example, in U.S. Pat. Nos. 4,683,195 and 4,683,202.

The PCR amplification method may be combined with a prior step of reverse transcription in order to amplify an RNA sequence in the form of DNA.

The polymerase chain amplification reaction coupled to reverse transcription (often designated in abbreviated form by the acronym RT-PCR) is now widely used to monitor gene expression at messenger RNA (mRNA) level, as well as for the direct cloning of coding sequences.

The polymerase chain amplification reaction coupled to reverse transcription hence consists in carrying out the synthesis of a first strand of complementary DNA (cDNA) using a reverse transcriptase, in denaturing the RNA-cDNA heteroduplex formed, in synthesizing a second cDNA strand, complementary to the first strand, under the action of a DNA polymerase, and in then subjecting the double-stranded cDNA obtained to a polymerase chain amplification according to known methods, which consist of a series of successive reactions of denaturation of the double-stranded DNA followed by its replication under the action of a DNA polymerase.

More specifically, the synthesis of the first cDNA strand is carried out using nucleoside triphosphates, by elongation of an oligonucleotide primer under the action of a reverse transcriptase. Since the copying of the RNA template takes place in the 3'Λ5' direction of the template, the oligonucleotide primer must be capable of hybridizing with a sequence located in the vicinity of the 3' end of the RNA to be copied. For this reason, the primer used in the reverse transcription operation is referred to as a 3' primer.

To carry out the synthesis of the second complementary DNA strand, the procedure is to synthesize the elongation product of a second primer capable of hybridizing with a sequence adjoining the 3' end of the first cDNA strand. In other words, the second primer must be identical to a sequence adjoining the 5' end of the starting RNA, or must be sufficiently homologous with such a sequence to be capable of hybridizing with said sequence of the first cDNA strand. For this reason, this second primer is referred to as a 5' primer.

The sequence to be amplified is hence flanked by the two primers.

Regardless of the methodology used, the RT-PCR reaction entails several successive reaction steps, namely denaturation of the RNA, hybridization of the 3' primer with the RNA, synthesis of a first cDNA strand using an enzyme possessing RNA-dependent DNA polymerase (or reverse transcriptase) activity, denaturation of the RNA-cDNA heteroduplex formed, hybridization of the 5' primer with the first cDNA strand, synthesis of the second cDNA strand using an enzyme possessing DNA-dependent DNA polymerase activity, and then the succession of amplification reactions by denaturation of the double-stranded DNA, hybridization of the 3' and 5' primers with the strand to which they are respectively complementary and synthesis of the second DNA strands by elongation from the primers.

The RT-PCR method is very sensitive. This great sensitivity is, moreover, often the source of "false-positive" results, caused by residual traces of genomic DNA in the mRNA preparations. For similar reasons, it is very important to avoid the accidental introduction of contaminating sequences. It is hence desirable to reduce to a minimum the risks of contamination during the succession of reactions constituting the chain amplification. However, depending on the methodology used, various manipulations may be required during the reaction, increasing the risk of introduction of contaminating sequences.

In its least sophisticated implementation, the RT-PCR method entails three steps, namely:

1) denaturation of the RNA by heating;

2) synthesis of the first cDNA strand in a buffer containing, apart from the nucleoside triphosphates, a 3' primer and a reverse transcriptase; and 3) synthesis of the second cDNA strand by addition of the 5' primer and a DNA polymerase, followed by the succession of amplification reactions by PCR; see, for example, Stefan SCHWARTZ, Journal of Virology, Vol. 64, No. 6, Jun. 1990, pp. 2519–259.

With the aim of simplifying the method and of reducing the number of manipulations, a simplified method has been described, based on the discovery of a common buffer for the reverse transcriptase and for Taq DNA polymerase. This simplified method consists: 1) in denaturing the RNA in aqueous solution, the two primers, 3' and 5', already being present, and 2) in adding the ingredients of the buffer, the reverse transcriptase and the DNA polymerase to the aqueous solution. Then, without subsequent addition of reactant, successive operations of synthesis of the first cDNA strand, denaturation of the RNA-cDNA duplex, synthesis of the second cDNA strand and amplification cycles are carried out at the various appropriate temperatures; see, in particular, C. GOBLET et al., Nucl. Acids Res., 17 (5), 2144 (1989). This method is improperly referred to as a "one-step method" whereas, in fact, as just seen, it entails two steps, since the denaturation and hybridization reaction is performed before adding the ingredients needed for the steps of reverse transcription and synthesis of double-stranded DNA, thereby increasing, just as in the conventional three-step method, the risk of introducing contaminating sequences.

Another technique has been developed, consisting in using a heat-stable enzyme (rTth) possessing both RNA-dependent DNA polymerase (reverse transcriptase) activity and RNA-dependent DNA polymerase activity. However, the first activity requires the presence of manganese ions while the second requires the presence of magnesium ions see MYERS T. W. et al., Biochem. 30, 7661–7666 (1991). It is hence necessary to perform the synthesis of the first cDNA strand in the presence of $MnCl_2$, followed by dilution of the sample with introduction of the 5' primer, $MgCl_2$ and a chelating agent which has the power to chelate manganese ions strongly. Here too, a process of dilution with introduction of reactants necessarily follows the synthesis of the cDNA, thereby increasing the risk of introducing contaminating sequences.

SUMMARY OF THE INVENTION

It has now been discovered that it is possible perform amplification coupled to reverse transcription a method genuinely requiring only a single manipulation step, that is to say a method in which all the reactants and solvents are all introduced right from the start into the reaction container, before the RNA denaturation step. This makes it possible to work in a simple manner and avoiding all risk of contamination on subsequent addition of reactants or solvents (the term solvent is used here to denote any liquid vehicle or any liquid constituent of the medium in which a reaction is carried out). In addition, it has been discovered that, surprisingly, this manner of working in a single step is more efficient than working according to the previous techniques, as will be shown in the experimental part below.

DETAILED DESCRIPTION OF PREFERRED EMBODIMENTS

The problem created by carrying out RT-PCR with introduction of all the reactants right from the start are associated, in particular, with the choice of a reverse transcriptase capable of functioning after being brought to a relatively high temperature during the step of heat denaturation of the RNA. This step of heat denaturation of the RNA is of very great importance for the success and reliability of an amplification method. In addition, after this heat treatment, the reverse transcriptase must still be capable of functioning at a relatively high temperature. It is known, in effect, that, in order to increase the specificity of the amplification reaction, it is helpful to work under sufficiently discriminating conditions, that is to say, in particular, at the highest possible temperature, so as to prevent a non-specific pairing of the 3' primer which would run the risk of bringing about the amplification of a sequence other than the target sequence, and also to work at a sufficiently high temperature to avoid renaturation of the RNA to be amplified.

It is also necessary for the DNA-dependent DNA polymerase to withstand heat, this applying also during the step of denaturation of the RNA-cDNA heteroduplex which requires high temperatures, generally above 90° C. This problem has, in fact, already been solved, since the use has been described of a DNA polymerase originating from microorganisms which are capable of surviving under high temperature conditions, and especially Taq polymerase which is capable of withstanding temperatures of the order of 95° C.

A heat-stable reverse transcriptase capable of playing, in addition, the part of DNA polymerase is already known, as pointed out above, but it requires a modification of the ionic environment in order to exert the second function (see MYERS et al., paper cited above). Hence such an enzyme cannot be used in a method in which all the ingredients have to be introduced together right from the start.

It has now been discovered that some reverse transcriptases which are not renowned for their heat stability are capable, when used in a sufficient quantity, of functioning at relatively high temperatures even after undergoing the heat treatment needed for the RNA denaturation step.

The subject of the present invention is hence a method for the amplification of at least one specific sequence of RNA contained or likely to be contained in a sample, comprising the steps consisting in:

obtaining a starting solution containing the RNA of said sample in a suitable buffer, denaturing the RNA contained in said solution by heating, treating the solution obtained, containing the denatured RNA, with a first primer (or 3' primer) under conditions permitting hybridization of the primer followed by the synthesis of a first DNA strand complementary to the RNA sequence to be amplified, in the presence of a sufficient quantity of an enzyme system having reverse transcriptase activity in said buffer, denaturing the RNA-cDNA heteroduplex formed, and treating the solution obtained with a second primer (or 5' primer) under conditions permitting hybridization of the second primer followed by the synthesis of the second cDNA strand, in the presence of a heat-stable enzyme system having DNA polymerase activity in the same buffer, and subjecting the cDNA obtained to a sufficient number of amplification cycles to obtain the desired degree of amplification, wherein said solution contains, right from the start, all the reactants and solvents needed for said steps, wherein all the steps are performed in the same container and without addition of reactants or solvents, and wherein the denaturation of the RNA is performed at a temperature of not less than approximately 60° C.

The starting solution is generally a suitable aqueous buffer that enables the reverse transcriptase and the DNA polymerase to function, for example a Tris buffer having a pH of 7 to 8.5, and preferably higher than 8. This starting solution contains, in particular, the ions needed for the reverse transcriptase and DNA polymerase activities, in particular alkali metal (Na, K) ions, introduced, for example, in the form of salts such as a chloride, at a concentration which can range from 20 to 50 mM, and magnesium ions, introduced, for example, in the form of a magnesium salt such as the chloride, at a concentration which can range, in particular, from 1 to 6 mM, for example from 1 to 5 mM. It can contain, in addition, various common ingredients, for example those used in the experimental part below.

The starting solution can contain, for example, from 2.5 ng to 1 lg of total RNA of the sample to be amplified, for a final volume of 100 ll. The RNA can, for example, be dissolved in the liquid medium, or be introduced into the latter in the adsorbed state on a suitable solid support.

The starting solution contains, of course, a sufficient quantity of nucleoside triphosphates to permit the synthesis of the complementary DNA, as well as the synthesis of the DNA strands when the amplification method is of the PCR type, the nucleoside triphosphates may be replaced completely or partially by modified and/or labelled nucleosides permitting elongation of the strands to be synthesized from the primers.

A critical point in the amplification of RNA lies in the secondary structures of RNA, which can induce early terminations during the reverse transcription step. For this reason, the amplification begins with an RNA denaturation step which can be carried out, for example, by heating to a temperature generally above 60° C., for example of between 60° and 75° C, for 1 to 15 minutes. The optimal conditions, which vary, in particular, according to the nature of the RNA, maybe determined in each case by simple routine experiments. It is preferable to work at a temperature equal to at least 65° C.

The 3' primer is generally a DNA primer. The choice of primer is determined by known criteria. It is possible to use an oligo (dT) oligonucleotide primer. For greater specificity, when the sequence of the gene is known or when the sequence of the corresponding protein is known, the localization of the 3' primer may be chosen more precisely. In particular, the problems associated with a possible contamination with DNA may be overcome in some cases by selecting primers located in separate exons or straddling junctions of splicing sites, thereby inducing in the first case coamplification of the DNA and the RNA, and readily separable amplification products of different sizes are then obtained, and in the second case exclusive amplification of the RNA. Lastly, in some cases, there will be reasons for choosing oligonucleotide primers which are not strictly complementary to the target, for the amplification of unidentified endogenous viruses or of unknown sequences that are theoretically closely related to known sequences; this is the case, in particular, when testing for the presence of an unknown retrovirus: a 3' primer complementary to a sequence which is generally well conserved in retroviruses, for example a sequence of the "pol" region, may then be used.

Preferably, the 3' primer has a sufficient length (in number of nucleotides) to be capable of hybridizing with the RNA at the chosen denaturation temperature. The force of adhesion of a DNA hybridized to an RNA or to a DNA is known to depend on the nature of the bases and on the number of bases paired. When the hybridization duplex is heated, a rupture of the hydrogen bonds between the bases takes place at a certain temperature, with separation of the two strands at this temperature, termed the denaturation temperature or melting temperature. This denaturation temperature increases with the number bases, and more precisely with the number of fully paired bases. In the present case, it is generally desirable to be able to obtain a hybridization of the 3' primer at the denaturation temperature of the RNA in order to prevent a renaturation of the RNA during this hybridization step. For the same reason, it will generally be preferable to cool rapidly, at the end of the RNA denaturation step, to the temperature at which the reverse transcription step will be performed.

Generally, the 3' primer contains at least 15 nucleotides, and especially from 15 to 30 nucleotides, or more when it is possible to work at high temperature, the choice of the high temperature depending, in particular, on the capacity of the reverse transcriptase to withstand said temperature.

It is possible to determine by simple routine experiments the temperature and duration of the heat treatment which the reverse transcriptase is capable of withstanding without significant loss of activity. The denaturation of the RNA and the hybridization of the 3' primer may hence be performed for a sufficient time to permit hybridization, but not longer than a predetermined period beyond which the enzyme system having reverse transcriptase activity would run the risk of being inactivated.

It should be noted that the 3' primer can contain, in the region of its 5' end, a non-specific oligonucleotide tail which does not participate in the hybridization with the target, that is to say with the RNA to be amplified. This non-specific tail can contain, for example, in a known manner, a restriction site (which facilitates a subsequent cloning), a promoter sequence (which facilitates a subsequent transcription) or any particular sequence capable of furthering a subsequent process of replication.

After the denaturation and hybridization step, the solution may be cooled, preferably rapidly, to a predetermined temperature permitting implementation of the reverse transcriptase activity, said temperature being sufficiently high to prevent renaturation of the RNA and also to maintain the hybridization of the 3' primer under sufficiently discriminating conditions, that is to say sufficiently high to prevent any insufficiently specific hybridization of the 3' primer, on the understanding that the reverse transcriptase must be able to exert its activity at the chosen temperature.

The temperature chosen for the reverse transcription step is preferably equal to at least 45° or 50° C. approximately, and for example between 50° and 75° C. approximately, in particular between 50° and 65° C., and especially between 50° and 60° C.

When the RNA sequence to be amplified is unknown or known only imperfectly, and a 3' primer which is not strictly complementary to the target is then used, it is desirable for the solution to be cooled, after the RNA denaturation step, to a sufficiently low temperature to permit hybridization of the 3' primer to an RNA sequence which is not absolutely complementary, but for a sufficiently short time to prevent purely random or non-specific hybridizations, after which the solution is heated to the predetermined temperature chosen for the reverse transcription step. In this case, the solution is cooled to a temperature below 50° C. but equal to at least 40° C., trials being carried out, for example, at increasingly low temperatures. The temperature can then be raised to that chosen for the reverse transcription step; the choice of this temperature has already been discussed above.

The duration of the reverse transcription step obviously depends on the length of the RNA strand to be amplified. It will be advantageous to choose the shortest, but sufficient, time that permits a cDNA strand having a sufficient length to contain at least the sequence complementary to the second primer (5' primer) to be obtained. Where possible, the duration of the reverse transcription operation will be determined by routine experiments. In other cases, this time will have to be estimated, taking care, in particular, not to work at too high a temperature or for excessively long times so as to avoid phenomena of "fatigue" (loss of efficiency) of the reverse transcriptase when the RNA sequence is relatively long.

The duration of the step of synthesis of the first cDNA strand will generally be less than 15 minutes. Preferably, this duration can vary from 1 to 10 minutes approximately.

For the reverse transcription operation, a reverse transcriptase which is not renowned for its heat stability may be used, chosen after simple experiments permitting determination of the heat treatments which the enzyme under study is capable of withstanding (within the context defined above), thereby enabling the reverse transcriptases which can be used in the method of the invention to be selected. It was, in effect, discovered, as already mentioned above, that reverse transcriptases which are not renowned for their heat stability were, in fact, sufficiently heat stable to be capable of being used in an RNA amplification method with introduction of all of the reactants into the starting solution.

The reverse transcriptase may be chosen, for example, from the reverse transcriptases of avian myeloblastosis virus (abbreviated to RT-AMV) and the reverse transcriptases of Moloney murine leukemia virus (abbreviated to RT-MMuLV). There may be mentioned, for example, RT-AMVbo (Boehringer Mannheim), RT-AMVbrl (Bethesda Research Laboratory), RT-MMuLVss (Bethesda Research Laboratory), and the like.

As mentioned above, the reverse transcriptase must be used in a sufficient quantity to permit, after heat denaturation treatment of the RNA, the first cDNA strand to be obtained under the chosen conditions. This sufficient quantity generally corresponds to an excess relative to the DNA polymerase.

The quantity (or concentration) of the reverse transcriptase may be determined in each case by routine experiments. It can vary, for example, from 5 to 200 U, in particular 5 to 20 U, for RT-AMV, and 100 to 200 U for RT-MMuLV, for a final volume of 100 ll. Generally, in the method of the invention, quantities of reverse transcriptase and of DNA polymerase are used such that their ratio, expressed in RT-AMV and Taq polymerase units, respectively, is equal to at least 2, and especially equal to at least 3, and is less than 8, especially less than 7, and can vary, in particular from 2 to 6, or, when a reverse transcriptase and/or a DNA polymerase other than RT-AMV and Taq polymerase, respectively, is/are chosen, these enzymes are used in quantities such that equivalent quantities of RT-AMV and of Taq polymerase, respectively, are in the same ratio equal to at least 2 and less than 8.

After the reverse transcription operation, the RNA-cDNA heteroduplex formed may be denatured by heating to a sufficient temperature, for example a temperature above 90° C. Naturally, it will then be appropriate to use, for the purpose of the subsequent DNA amplification operations, a DNA polymerase capable of withstanding such a temperature, such as, for example, Taq polymerase, rTth (Cetus), Pfu DNA polymerase (Stratagene), Vent polymerase (Biolabs), and the like.

After the step of denaturation of the RNA-cDNA hybrid, the temperature is lowered so as to permit hybridization of the second primer (5' primer). Here too, this hybridization temperature will preferably be chosen to be fairly high, for example equal to at least 50° C., and in particular from 50° to 80° C., so as to permit hybridization under sufficiently discriminating conditions.

The criteria for choosing the 5' primer and its length are obviously the same, making the necessary adjustments, as those described above for choosing the 3' primer, and when the 5' primer is a primer which is not strictly complementary to the target, the solution may be cooled, as above, to a sufficiently low temperature (for example below 50° C., and in particular between 40° and 50° C.) to permit hybridization of the 5' primer to a DNA sequence which is not absolutely complementary, for a sufficiently short time to prevent purely random or non-specific hybridizations, after which the solution will be heated to a predetermined temperature chosen for the step of synthesis of the second cDNA strand.

This step of synthesis of the second cDNA strand is performed at a sufficiently discriminating temperature, that is to say a temperature which is sufficiently high but which remains compatible with maintenance of the specific hybridization of the 5' primer, especially a temperature of at least 50° C. (for example from 50° to 80° C. approximately). The steps of hybridization of the primer with the first cDNA strand and of synthesis of the second cDNA strand may be performed at the same temperature.

The 3' and 5' primers may be used, for example, in substantially equimolar quantities. These primers, which can consist of RNA or of DNA, are used in large excess, as is known for amplification reactions. The 5' primer can contain a non-specific oligonucleotide tail at its 5' end, as already explained above in relation to the 3' primer.

After the step of synthesis of the second cDNA strand, the double-stranded cDNA obtained may be subjected to a sufficient number of amplification cycles according to known methods, for example by denaturation of the double-stranded DNA, hybridization of the 3' and 5' primers with the newly formed DNA strands to which they are respectively complementary and synthesis of elongation product under the action of the DNA polymerase. Such amplification cycles may be performed according to known methods by simple heat treatments at various temperatures, for example a temperature of 90°–98° C. approximately for the denaturation of double-stranded DNA, a temperature of 40°–80° C. approximately for the hybridization of the primers and a temperature of 60°–80° C. approximately for the synthesis of the elongation products. These amplification cycles, like all the steps of the method of the invention, may be carried out automatically in commercially available programable equipment.

The method of the invention is applicable, in particular, to the diagnosis of viral or bacterial infections and of genetic disorders. It is also applicable to bacterial or viral typing, and to cell typing including HLA. It is applicable as well to the cloning of unidentified endogens or of unknown RNA sequences which are theoretically closely related to but different from known sequences, using the step of hybridization at a sufficiently low controlled temperature between the RNA denaturation step and the synthesis of the cDNA. The method of the invention also makes it possible to amplify RNA in situ on tissue (for example on fixed tissue, on frozen tissue or on suitably prepared smears) deposited on or attached to a support, the boundaries of the reaction compartment being, for example, defined by the supporting slide to which the tissue is attached and a sealed coverglass, as was done for DNA amplification; see Nuovo G. J. et al., Am. J. Pathol., 139, 847–854 (1991).

The method of the invention may be used to carry out coamplifications, either with different primer systems or with a common 3' primer.

The method of the invention can, in particular, be used to carry out the quantification of a target RNA, either directly relative to a standard series, or by coamplification, according to known methods, with an internal standard introduced in a controlled quantity and which can be amplified using the same primers as the target RNA; see, for example, the documents PCT/US90/04707 and Michael Becker-André et al., Nucleic Acids Research, Vol. 17, pp. 9437–9447 (1989).

The invention also relates to the use as a probe (in a method for the detection of the HIV-1 virus) or as a primer (in any method for the amplification of HIV-1 virus RNA, including a method as described in the present patent application), of an oligonucleotide sequence:

comprising the sequence

CCTATCTGTCCCCTCAGCTAC (SEQ ID NO: 1)

which can be used, in particular, as a 3' primer, or comprising the sequence

TCTATCAAAGCAACCCAC (SEQ ID NO: 2)

which can be used, in particular, as a 5' primer.

The advantages obtained by using these sequences become apparent from the experimental part below.

The subject of the invention is also purified oligonucleotides containing, for example, approximately 30 nucleotides at most, and containing one of the two sequences which have just been defined. Said purified oligonucleotides can contain, at one of the ends, at least, of the minimum sequence shown, nucleotides which may be chosen from those flanking said sequence in the complementary DNA corresponding to HIV-1 RNA. Said purified oligonucleotides can also contain a non-specific oligonucleotide tail at their 5' end, as explained above in relation to the amplification primers. The purified oligonucleotides of the invention can also contain modified nucleotides or nucleotides labelled with a tracer agent. They may be used, in particular, as capture or detection probes in a method of diagnosis of HIV-1 infections, and/or as amplification primers. They may be prepared according to conventional methods of oligonucleotide synthesis.

The invention will now be further illustrated by means of the experimental part given below. In the examples which follow, the primers may be referred to as "amplimers" as well as "primers", and the 3' primer may also be referred to as a "reverse primer". The DNA transfer technique, termed Southern transfer, from a gel, for example after electrophoresis, onto a membrane on which the DNA may be hybridized with a labelled nucleic acid probe, is designated by the expression "Southern blot". The RNA transfer technique termed Northern transfer is designated in a similar manner. In these examples, reference will be made to the attached drawings, wherein:

EXPERIMENT PART

Figure 1:
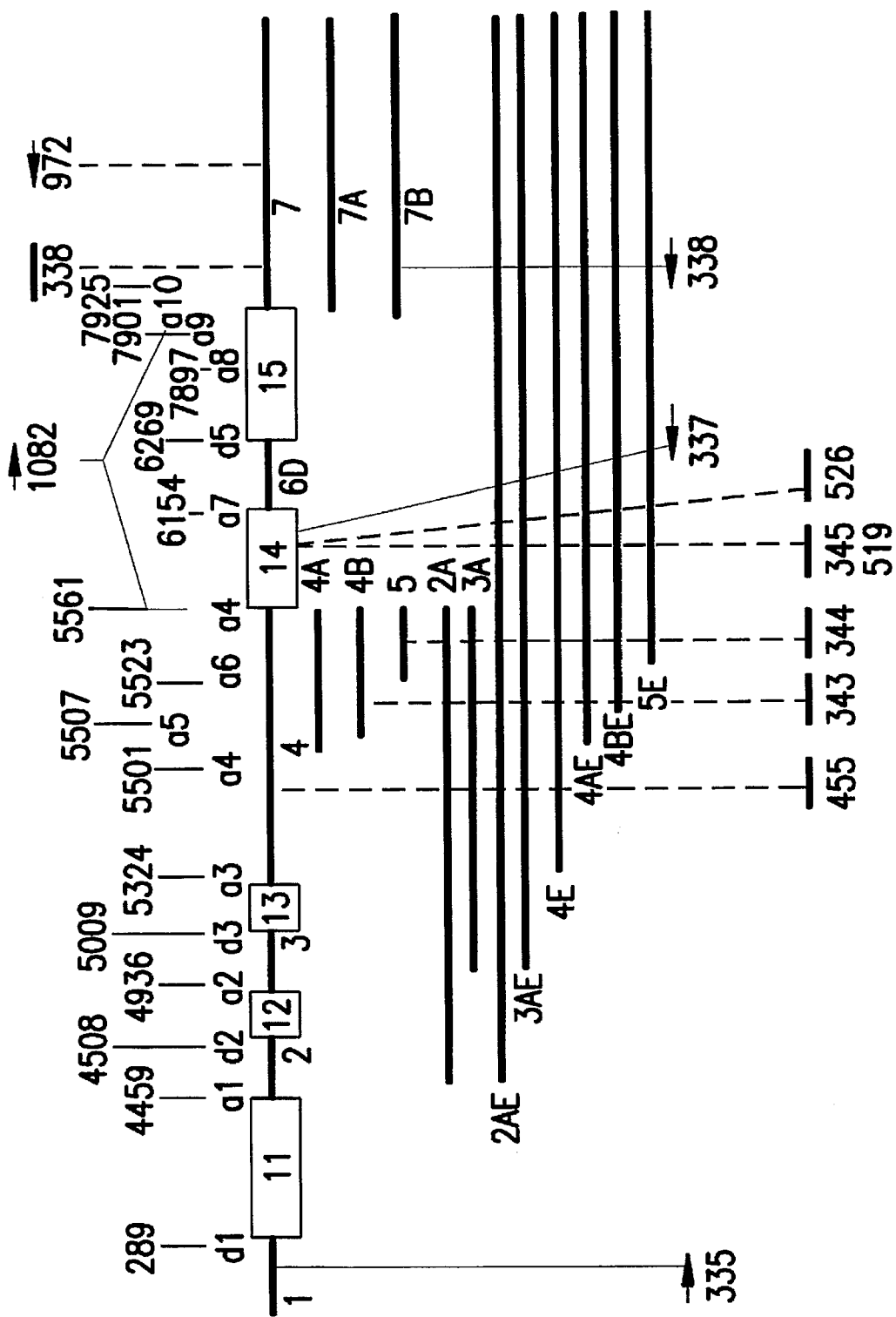
FIG. 1 is a diagram of the organization of the messenger RNAs of HIV-1, the probes or primers employed being indicated.

The biological model studied in this experimental part is the RNA of the human immunodeficiency virus, HIV-1. The structure of the mRNAs of the virus, and especially the localization of the splicing donor (d1 to d4) and acceptor (a1 to a10) sites, the nomenclature of the exons (bold lines labelled 1 to 7 with characterization A, B, D, AE, BE or E) and introns (i4 to i5) as well as the localization of the 5' amplimers (arrow pointing right), the reverse primers/3' amplimers (arrow pointing left) and the probes (bold rectangles) are itemized in FIG. 1. The oligonucleotide primers and probes were synthesized on an Applied Biosystem 394 DNA/RNA synthesizer, analyzed and purified in reversed-phase HPLC where necessary. They are listed in Table 1 below. The numbering used in FIG. 1 and the table follows the nomenclature of the molecular clone HIV-HXB2R (Lawrence, J., et al., 1990, edited by Myers, G., et al.).

Table 1: oligonucleotide primers and probes
Amplimers and reverse primers
Analysis of multispliced mRNAs
*335 (171–189) 5' amplimer: ATCTCTAGCAGTG-GCGCCC (SEQ ID NO: 3)
*338 (7967–7949) 3' amplimer and reverse primer: TTC-CTTCGGGCCTGTCGGG (SEQ ID NO: 4)
Analysis of monospliced mRNAs
*335 (171–189) 5' amplimer: ATCTCTAGCAGTG-GCGCCC (SEQ ID NO: 3)
*337 (5933–5912) 3' amplimer and reverse primer: CACAAAATAGAGTGGTGGTTGC (SEQ ID NO: 5)
Analysis of mRNAs using the d4-a10 splicing sites
*1082 (5580–5591 to 7925–7930) 5' amplimer: TCTATCAAAGCA-ACCCAC (SEQ. ID NO: 2)
*972 (8254–8234) 3' amplimer and reverse primer: CCTATCTGTCCCCTCAGCTAC (SEQ ID NO: 1)
Probes
*344 (5540–5524) Exon 5: TCGTCGCTGTCTCCGCT-TCTTC (SEQ ID NO: 6)
*343 (5526–5507) Exon 4B: CTTCCTGCCATAG-GAGATGC (SEQ ID NO: 7)
*455 (5382–5359) Exon 4: CTCCATTTCTTGCTCTC-CTCTGTC (SEQ ID NO: 8)
*345 (5654–5676) Intron 4: CCACACAACTATTGCTAT-TATTA (SEQ ID NO: 9)
*338 (7967–7949) Exon 7: TTCCTTCGGGCCTGTCGGG (SEQ ID NO: 4)
*519 (5524–5541) Exon 5: AAGAAGCGGAGACAGCGA (SEQ ID NO: 10)
*526 (5754–5773) Intron 4: AGCAGAAGACAGTG-GCAATG (SEQ ID NO: 11)

EXAMPLE 1

Efficiency and sensitivity of the one-step method

Figure 2:
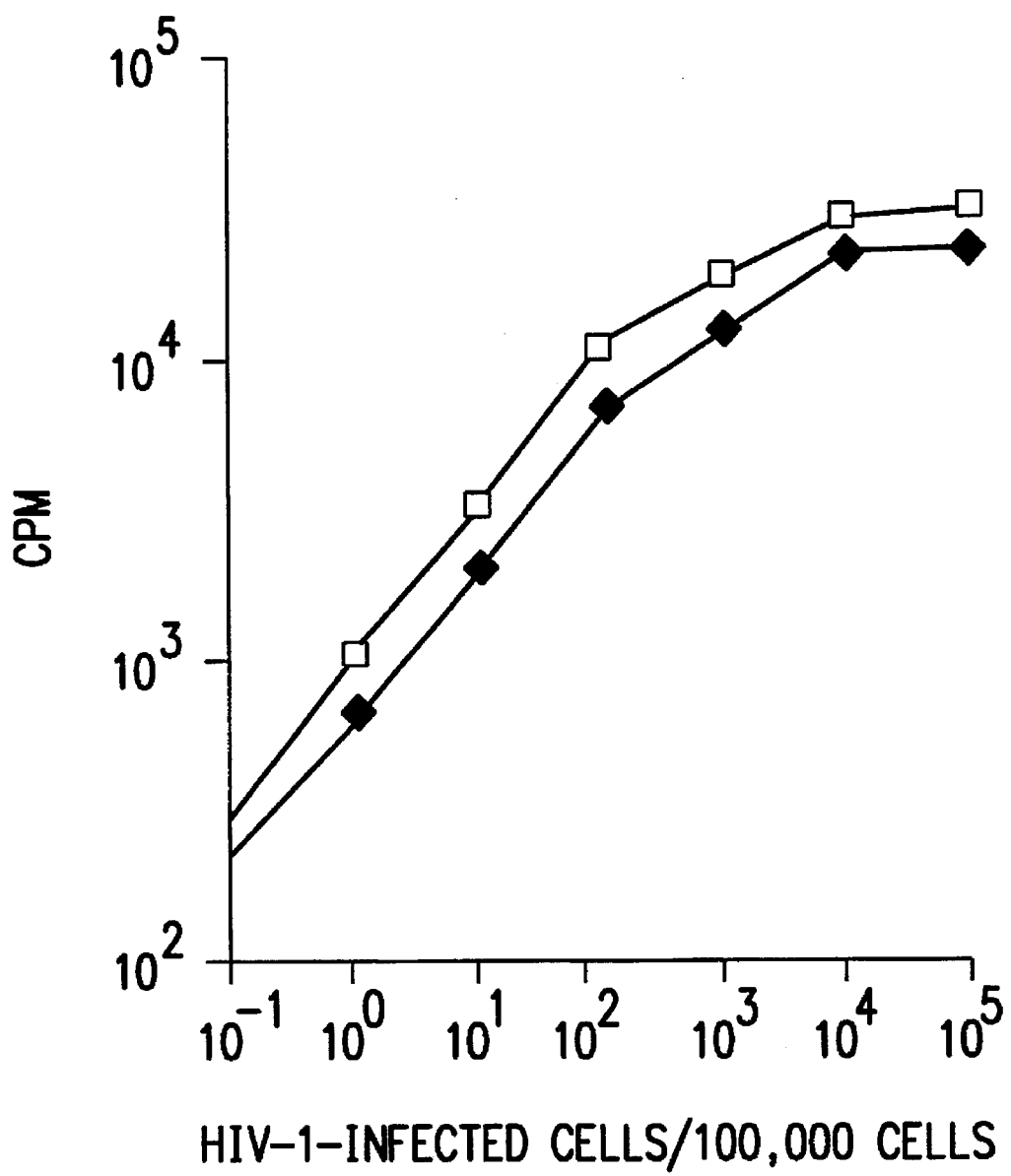
FIG. 2 shows the signal observed, in counts per minute (cpm), after amplification according to the procedure described in Example 1, as a function of the initial percentage of cells infected (two independent manipulations)

To determine the sensitivity of the amplification method in a single manipulation step, we defined a pair of amplimers, using the junctions of the d4-a8 acceptor sites of the HIV-1 virus (Tat exons 1-4-7, Rev exons 1-4A-7, Nef exons 1-5-7, FIG. 1), leading to the specific amplification of multispliced mRNAs of the HIV-1 virus (the splicing aspect of HIV-1 will be elaborated upon subsequently in Example 9). 1 ll of RNAguard (Pharmacia LKB Biotechnology) is added as an RNase inhibitor to all the samples, the latter containing 1 lg of RNA. The RNAs were extracted from lymphoid line H9 infected with the strain HTLV-IIIB, by the so-called guanidinium isothiocyanate technique (Chirgwin J. M., et al. 1979. Biochem 18:5294–5299) followed by cesium chloride gradient ultracentrifugation (Gilsin V., et al. 1973. Biochem 13:2633–2638). The final concentration of the buffer used is 10 mM Tris pH 8.3, 50 mM KCl, 1.5 mM $MgCl_2$, 0.01% gelatin. The final concentrations are: 310 nM amplimers, 250 lM dNTPs, 2.5 U Taq polymerase (Perkin Elmer-Cétus), 10 U RT-AMV (Boehringer-Mannheim). The amplification protocol, carried out in a thermocycler, consists of an incubation for 10 minutes at 65° C. (denaturation of the RNA and hybridization of the reverse primer, which is itself identical to the 3' amplimer), then 8 minutes at 50° C. (reverse transcription), then 5 minutes at 95° C. (denaturation of the DNA/RNA hybrids and inactivation of the reverse transcriptase), and then, consecutively, 35 PCR cycles are thereafter carried out, one cycle consisting of 1 minute at 95° C. for denaturation of the DNA, 1 minute at 55° C. for hybridization of the amplimers with the single-stranded DNA templates and 1 minute at 72° C. for elongation of the oligonucleotide primers (amplimers); the final cycle possesses, in addition, a 7-minute extension of the elongation step in order to terminate the synthesis of the incomplete DNA fragments. The RT-PCR products are then analyzed by Southern blotting. They are analyzed on 5% acrylamide gel, the DNA is then heat denatured by immersing the gel in boiling water for 5 minutes, and the gel is then equilibrated in a transfer buffer (89 mM Tris base, 89 mM boric acid, 2 mM EDTA, pH 8.0). The DNA then undergoes an electric transfer (1 hour, 300 mA, 4° C.) onto a nylon membrane and is fixed with UV. Prehybridization is carried out overnight at 42° C. in a buffer comprising 5*SSC, 0.1% SDS, 5* Denhart, 0.2 mg/ml salmon sperm DNA, 18% deIonized formamide, and hybridization is carried out for 4 hours at 50° C. in the abovementioned buffer containing $10^6$ cpm/ml of the oligonucleotide probe labelled with [$^{32}$P]-ddATP using the enzyme terminal transferase (Boehringer Mannheim), at a specific activity of $10^6$ cpm/mg. The filters are then washed in 1* SSC, 0.1% SDS for 10 minutes at room temperature and 10 minutes at 50° C., and thereafter developed by autoradiography for 3 hours at −80° C. Southern blot analysis of RNAs amplified with the primers 1082–972 (see Table 1 and FIG. 1) detects in autoradiography the expected 340-bp band, visualized with the probe 338 (Table 1, FIG. 1). No signal could be observed either in the absence of RT or when the PCR was carried out in the presence of 1 lg of DNA extracted from HTLV-IIIB-infected cells, as expected. A weak band, observed after 4 hours of autoradiography at −80° C., proves that the RNA specific to HIV can be detected when one cell out of $10^6$ is infected, using the one-step method according to the invention. The extraction yields permit the assertion that the RNA of approximately 0.1 infected H9 cell is present in the sample (1 lg of RNA) resulting from the final dilution used for the RT-PCR. The threshold of sensitivity of the assay is hence probably between 10 and 100 copies of a given target. The one-step assay was also tested for the potential quantification of RNA, using tenfold serial dilutions of the infected cells. A typical PCR curve representing the quantity of signal generated as a function of the proportion of cells infected was determined (FIG. 2): the result shows that, under these experimental conditions, the signal obtained shows a correlation with the initial concentration of target mRNA.

EXAMPLE 2

Comparisons of several RT-AMVs with several RT-MMuLVs

Figure 3:
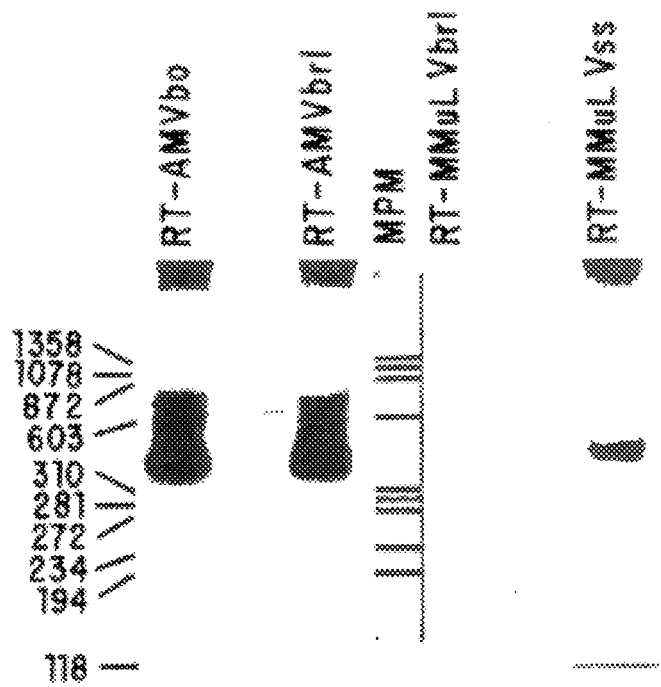
FIG. 3 is an autoradiographic picture obtained after amplification and Southern transfer according to the method of Example 2; the MWM (molecular weight markers) column represents molecular weight standards; the numbers shown in the left-hand column are numbers of nucleotides.

The experimental conditions used are essentially identical to those described in Example 1. The RNA is extracted from H9 cells infected with the strain HTLV-IIIB, the primers used are 335 and 337 and the enzymes are RT-AMVbm (Boehringer Mannheim) at 10 U per reaction, RT-AMVbrl (Bethesda Research Laboratory) at 10 U per reaction, RT-MMuLVbrl (Bethesda Research Laboratory) at 200 U per reaction and cloned RT-MMuLVss not possessing RNaseH (Bethesda Research Laboratory) at 200 U per reaction, the temperature cycles being 10 minutes at 65° C., 8 minutes at 50° C. and 5 minutes at 95° C., and then, consecutively, 35 PCR cycles are thereafter carried out, one cycle consisting of 1 minute at 95° C., 2 minutes at 55° C. and 2 minutes 30 seconds at 72° C.; the final cycle possesses, in addition, a 7-minute extension of the elongation step. Southern blot analysis (see Example 1) of RNAs amplified with the primers 335–337 (see Table 1 and FIG. 1) detects the expected preponderant band at 530 bp (FIG. 3), visualized with the probe 526 (Table 1, FIG. 1). The respective intensities of the signals show that RT-AMV has the greatest efficacy, irrespective of the source from which it has been obtained.

EXAMPLE 3

Influence of the addition of RNaseH with

Figure 4:
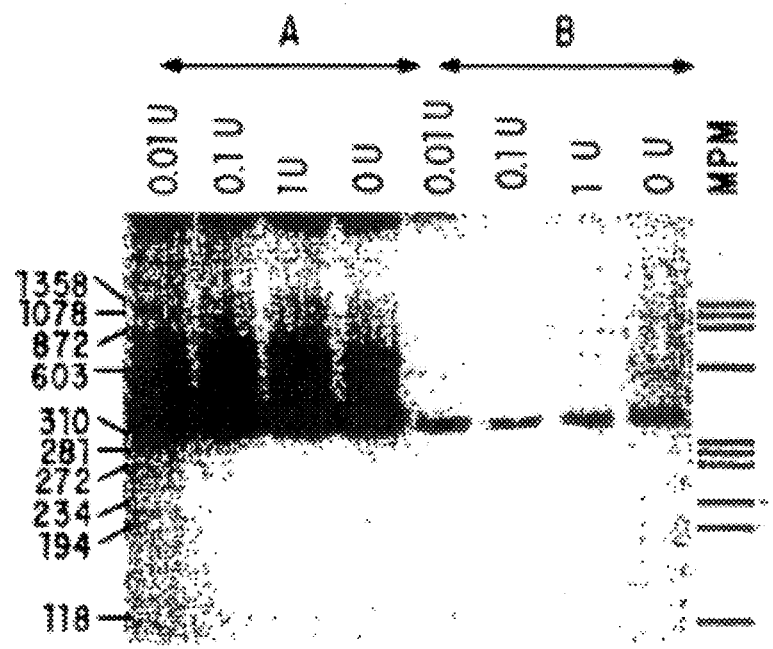
FIGS. 4 and 5 show the autoradiographic pictures obtained after amplification and Southern transfer, respectively, in Examples 3 and 4, respectively.

The experimental conditions used are essentially identical to those described in Example 1. The RNA is extracted from H9 cells infected with the strain HTLV-IIIB, the infected cells representing either 100% (A) or 1% (B) of the population treated. The primers used are 335–337, and the quantity of RNaseH (Boehringer Mannheim) is 1 unit, 0.1 unit, 0.01 unit and 0 unit as control. The temperature cycles used are identical to those described in Example 2 Southern blot analysis (sac Example 1) of RNAs amplified with the primers 335–337 (Table 1 and FIG. 1) detects the expected band at 530 bp (FIG. 4), visualized with the probe 526 (Table 1, FIG. 1). No appreciable difference is observed, regardless of the initial quantity of target RNA. It may also be noted that, regardless of the fact that RT-MMuLVss (RNaseH-minus) is less efficient than the RT-AMVs (Example 2, FIG. 3), it is, however, appreciably more efficient than the uncloned RT-MMuLVs possessing RNaseH activity (Example 2, FIG. 3). These results show collectively that the efficiency of the method is not due to RNAseH activity present in the reaction tube.

EXAMPLE 4

Temperature kinetics

Figure 5:
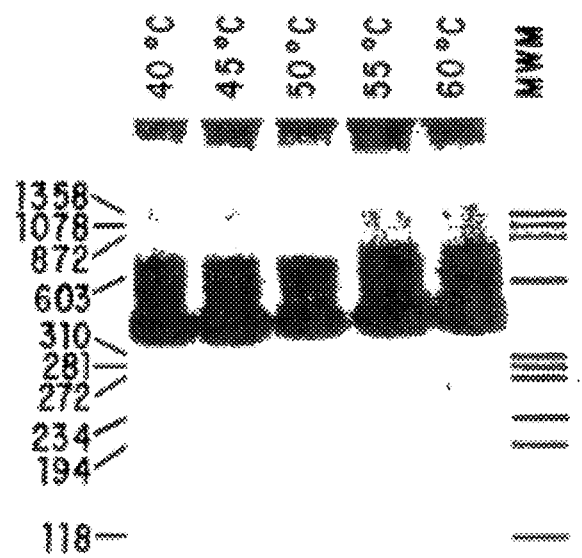

The experimental conditions used are essentially identical to those described in Example 1. The RNA is extracted from H9 cells infected with the strain HTLV-IIIB, and the primers used are 335–337. The amplification cycle, carried out in a thermocycler, consists of an incubation for 10 minutes at 65° C., and reverse transcription is then carried out for 8 minutes at different temperatures, 40° C., 45° C., 50° C., 55° C. and 60° C., respectively, then 5 minutes at 95° C., and, consecutively, 35 PCR cycles are thereafter carried out, one cycle consisting of 1 minute at 95° C., 2 minutes at 55° C. and 2 minutes 30 seconds at 72° C.; the final cycle possesses, in addition, a 7-minute extension of the elongation step. Southern blot analysis (see Example 1) of RNAs amplified with the primers 335–337 Table 1 and FIG. 1) detect the expected band at 530 bp (FIG. 5), visualized with the probe 526 (Table 1, FIG. 1). The respective intensities of the signals do not show an appreciable decrease in the efficiency of the amplification, and hence in the efficiency of RT-AMV, in a temperature range between 40° C. and 80° C. for 8 minutes in addition to the denaturation cycle at 65° C. for 10 minutes.

EXAMPLE 5

Positioning of Taq and of the 5' amplimer in the amplification reaction

Figure 6:
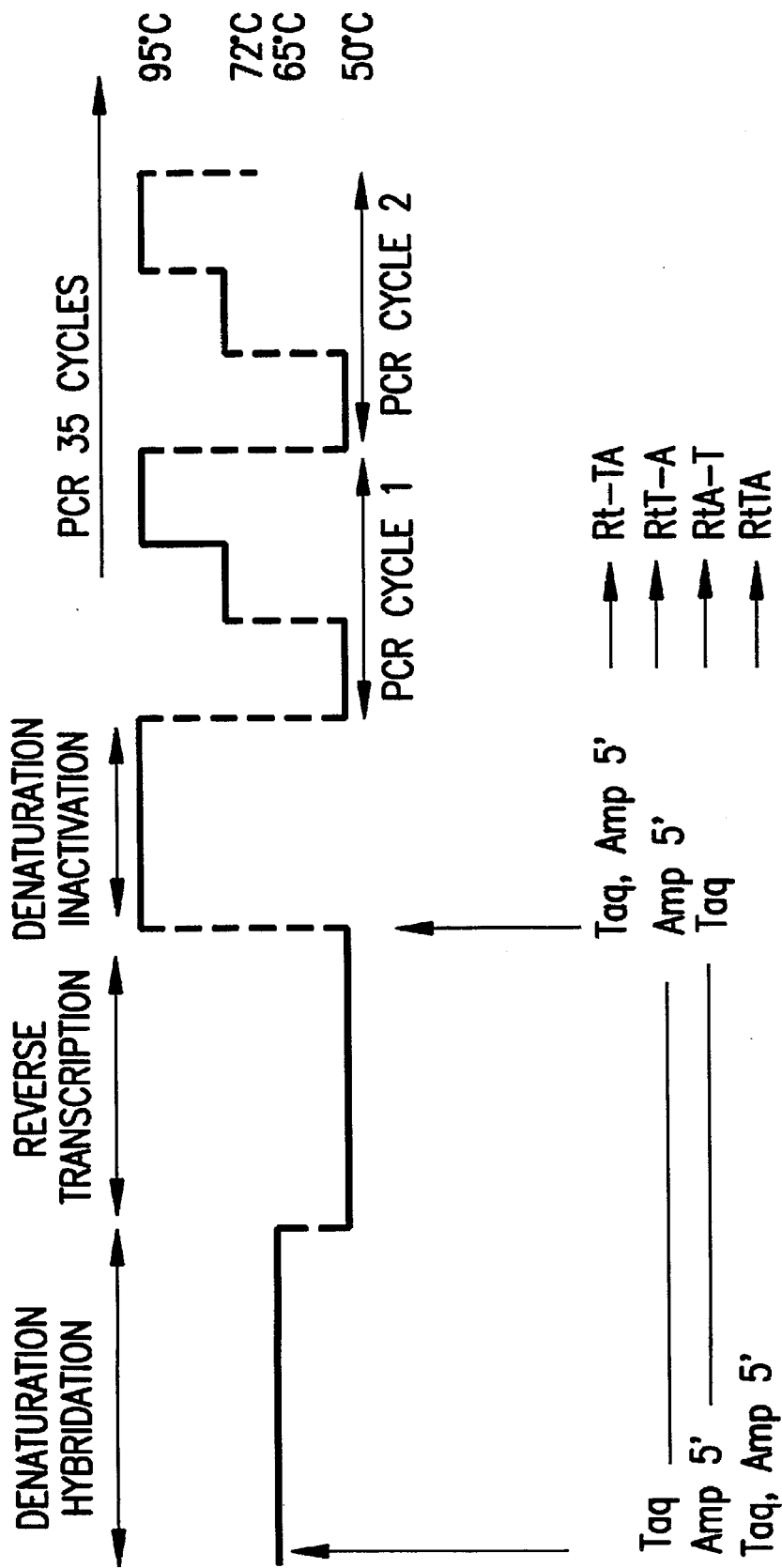
FIG. 6 is a diagram illustrating the temperature cycles used in Example 5, the time of introduction of the reactants being indicated.
Figure 7:
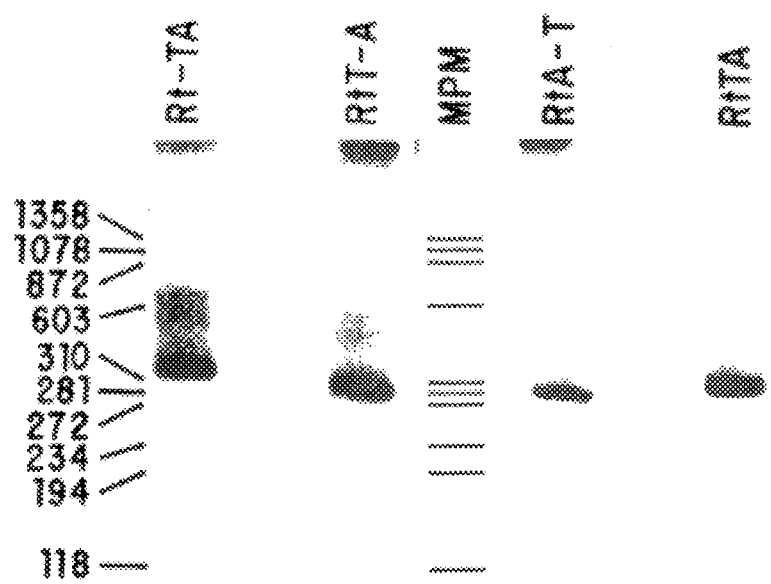
FIG. 7 is the autoradiographic picture obtained after amplification and transfer according to the method of Example 5; the references appearing in FIG. 7 correspond to the various procedures indicated in FIG. 6.

The experimental conditions used are identical to those described in Example 1. The RNA is extracted from H9 cells infected with the strain HTLV-IIIB and the primers are 335–337, Taq and/or the 5' amplimer being introduced into the reaction tube either right from the start of the reaction, or at the end of the step of synthesis of the cDNA for 8 minutes at 50° C. The four combinations were carried out and are made clear on the diagram in FIG. 6. The temperature cycles used are identical to those described in Example 2. Southern blot analysis (see Example 1) of RNAs amplified with the primers 335–337 (Table 1 and FIG. 1) demonstrates the expected preponderant band at 530 bp (FIG. 7), visualized with the probe 526 (Table 1, FIG. 1). No significant difference is observed, irrespective of the time of introduction of Taq and/of the 5' amplimer.

EXAMPLE 6

Influence of the time of introduction of RT

Figure 8:
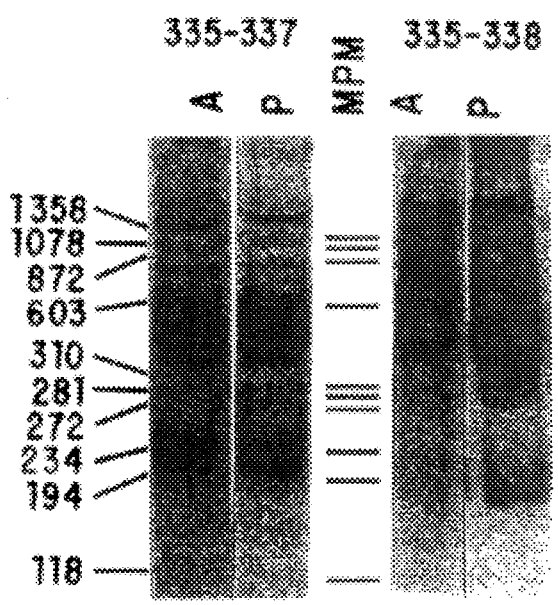
FIG. 8 is the autoradiographic picture obtained at the end of the method of Example 6.

The experimental conditions used are essentially identical to those described in Example 1. The RNA is extracted from H9 cells infected with strain HTLV-IIIB and the primers are 335–337 or 335–338. The temperature cycles used are identical to those described in Example 2. The reverse transcriptase is present in the reaction tube right from the start of the reaction (A) or is introduced after the denaturation/hybridization step at 65° C. (P). Southern blot analysis (see Example 1) of RNAs amplified with the primers 335–337 or 335–338 (Table 1, FIG. 1) detects the expected characteristic bands (FIG. 8), visualized with the probe 519 (Table 1, FIG. 1). In the case where the RT is introduced after the denaturation step, an increase in the non-specific signals may be noted especially for the amplification of highly structured mRNAs (335–338, column P), and the interpretation of this will be elaborated upon subsequently (see Example 9).

EXAMPLE 7

Influence of the quantity of 3' primer (reverse primer and amplimer)

Figure 9:
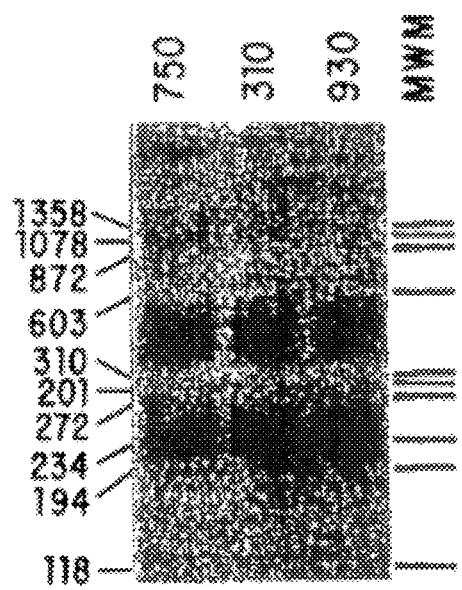
FIG. 9 is the autoradiographic picture obtained at the end of the method of Example 7; the references in the various columns correspond to the quantities (nM) of 3' primer.

The experimental conditions used are essentially identical to those described in Example 1. The RNA is extracted from H9 cells infected with the strain HTLV-IIIB, 250 ng of RNA are used as reaction substrate and the primers are 335–338, the quantity of reverse primer (338) being either 310 nM (equimolar with the 5' amplimer) or 930 nM. An assay was also carried out using the enzyme rTth with a concentration of 750 nM of the reverse primer and 150 nM of the 5' amplimer, according to a methodology described in section II (Myers T. W., et al. 1991. Biochem 30:7661–7666). The temperature cycles used are identical to those described in Example 2. Southern blot analysis (see Example 1) of RNAs amplified with the primers 335–338 (Table 1, FIG. 1) detects the expected characteristic bands (FIG. 9), visualized with the probe 519 (Table 1, FIG. 1). No difference is observed either qualitatively or quantitatively, irrespective of the quantity of reverse primer. Hence it does not appear to be necessary to use the latter in excess relative to the 5' amplimer.

EXAMPLE 8

Influence of the quantity of RNA in the reaction tube

Figure 10:
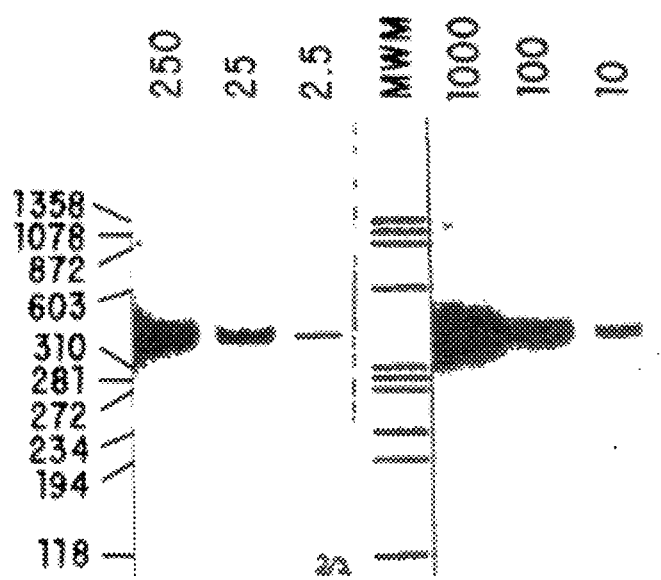
FIG. 10 shows the autoradiographic picture obtained at the end of the method of Example 8; the references in the columns correspond to the quantities of RNA in the sample analyzed (in ng); the line corresponding to the band observed in the original photograph of the 2.5 column has been intensified so as to be more visible on the reproductions of FIG. 10.

The experimental conditions used are identical to those described in Example 1. The RNA is extracted from H9 cells infected with the strain HTLV-IIIB, the infected cells representing 0.01% of the population treated. The quantity of total RNA used is 2.5, 10, 25, 100, 250 and 1000 ng. Southern blot analysis (see Example 1) of RNAs amplified with the primers 1082–972 (Table 1, FIG. 1) detects the expected 340-bp band (FIG. 10), visualized with the probe 338 (Table 1, FIG. 1). The signal obtained is proportional to the initial quantity of target RNA, and appears to be independent of the total quantity of RNA present in the reaction tube.

EXAMPLE 9

Comparison of the reaction parameters involved in RT-PCR

The relative efficiencies of the so-called "one-step" or "two-step" methods were compared, using both RT and Taq.

In the "two-step" method, we studied the influence of the parameters volume, buffer and temperature on the hybridization of the reverse primer as well as on the reverse transcription. The different RT-PCR protocols comprising, in addition, all the constituents involved in the reaction, their concentration and also the sequential order of their introduction are listed in Table 2. 1 ll of RNAguard (Pharmacia LKB Biotechnology) is added to all the samples, the latter containing 1 lg of RNA. The RNAs were extracted from promonocyte line U937 infected with the strain HIV-LAV.

In Table 2, each column corresponds to a particular embodiment used, depending on the primers employed, either for amplification of the Reg region or for amplification of the Env region. Each arbitrary sample number corresponds to a particular experiment. In all cases, denaturation of the RNA is performed by heating for 10 minutes to 65° C. It is either followed by a slow cooling (+) in the course of 30 minutes to 42° C., or the reaction is immediately linked up with the reverse transcription step (1) or the tube is rapidly cooled in ice (–). For the reaction of synthesis of the first cDNA strand (Extension), the time in minutes (except where otherwise stated) has been shown on the first line and the temperature in ° C. on the second line.

TABLE 2

| Sample | Reg<br>Env | 87<br>77 | 88<br>78 | K8<br>K7 | 81<br>71 | 82<br>72 | 83<br>73 | 84<br>74 | 85<br>75 | 86<br>76 |
|---|---|---|---|---|---|---|---|---|---|---|
| Description of RT-PCR procedures | | | | | | | | | | |
| HYBRIDIZATION (STEP 1) | | | | | | | | | | |
| RNA (1 g) | | 1 | 1 | 1 | 1 | 1 | 1 | 1 | 1 | 1 |
| BUFFER | | water | water | PCR*1 | PCR*1 | PCR*1 | PCR*1 | PCR*1 | PCR*1 | PCR*1 |
| MgCl$_2$ (mM) | | 0 | 0 | 1.5 | 1.5 | 1.5 | 1.5 | 1.5 | 1.5 | 1.5 |
| dNTP (1 M) | | 0 | 0 | 250 | 250 | 250 | 250 | 250 | 250 | 250 |
| 3' amplimer (nM) | | 1550 | 1550 | 310 | 310 | 310 | 310 | 310 | 310 | 310 |

TABLE 2-continued

Description of RT-PCR procedures

| Sample | Reg<br>Env | 87<br>77 | 88<br>78 | K8<br>K7 | 81<br>71 | 82<br>72 | 83<br>73 | 84<br>74 | 85<br>75 | 86<br>76 |
|---|---|---|---|---|---|---|---|---|---|---|
| 5' amplimer (nM) | | 0 | 0 | 310 | 0 | 0 | 0 | 0 | 0 | 0 |
| Taq:RT-AMV (U) | | 0 | 0 | 2.5:10 | 0 | 0 | 0 | 0 | 0 | 0 |
| Final Volume (1l) | | 20 | 20 | 100 | 97 | 97 | 97 | 97 | 97 | 97 |
| Denaturation | | | | | 10 min. −65° C. | | | | | |
| Cooling | | − | − | 1 | + | + | + | − | − | − |
| REVERSE TRANSCRIPTION (STEP 2) | | | | | | | | | | |
| BUFFER | | PCR*1 | PCR*3 | PCR*1 | PCR*1 | PCR*1 | PCR*1 | PCR*1 | PCR*1 | PCR*1 |
| MgCl$_2$ (mM) | | 1.5 | 4.5 | 1.5 | 1.5 | 1.5 | 1.5 | 1.5 | 1.5 | 1.5 |
| dNTP (1 M) | | 250 | 750 | 250 | 250 | 250 | 250 | 250 | 250 | 250 |
| AMV (10 U) | | + | + | added step 1 | + | + | + | + | + | + |
| Final Volume (1l) | | 98 | 33 | 100 | 98 | 99 | 98 | 98 | 98 | 98 |
| Extension | | 1 h 45 | 1 h 45 | 8 50 | 10 50 | 1 h 45 | 45* 42 | 10 50 | 1 h 45 | 45* 42 |
| Denaturation | | | | | 5 min. −95° C. | | | | | |
| PCR (STEP 3) | | | | | | | | | | |
| BUFFER | | PCR*1 | PCR*1 | PCR*1 | PCR*1 | PCR*1 | PCR*1 | PCR*1 | PCR*1 | PCR*1 |
| MgCl$_2$ (mM) | | 1.5 | 1.5 | 1.5 | 1.5 | 1.5 | 1.5 | 1.5 | 1.5 | 1.5 |
| dNTP (1 M) | | 250 | 250 | 250 | 250 | 250 | 250 | 250 | 250 | 250 |
| Taq 2.5 U | | + | + | added step 1 | + | + | + | + | + | + |
| 5' amplimer (310 nM) | | + | + | added step 1 | + | + | + | + | + | + |
| Final Volume (1l) | | 100 | 100 | 100 | 100 | 100 | 100 | 100 | 100 | 100 |

*followed by 15 minutes at 50° C.

Each sample is stored in ice before the introduction of reactants where this is required. Hybridization of the reverse primer (step 1) is carried out in water or in a buffer comprising 10 mM Tris pH 8.3, 50 mM KCl, 1.5 mM MgCl$_2$, 0.01% gelatin (referred to as PCR*1) or in a buffer comprising 30 mM Tris pH 8.3, 150 mM KCl, 4.5 mM MgCl$_2$, 0.01% gelatin (referred to as PCR*3), at 65° C., with or without slow cooling to 42° C. The reverse primers, 338 (Table 1, FIG. 1) for the multispliced RNAs (referred to as Reg in Table 2) and 337 (Table 1, FIG. 1) for the monospliced RNAs (referred to as Env in Table 2), are chosen as being identical to the 3' amplimer involved in the PCR reaction. The reverse transcription step is carried out in the presence of concentrations of MgCl$_2$ and of dNTPs suited either to the reverse transcriptase activity or to that of Taq polymerase, varying both the time (from 8 minutes to 1 hour) and the temperature (42° C. to 50° C.) of the cDNA synthesis reaction. The concentration of RT-AMV (Boehringer Mannheim) is 10 U for 1 lg of RNA. Before the PCR cycles are linked up, the cDNA/mRNA hybrids are denatured and the reverse transcriptase is inactivated by heating the sample to 95° C. for 5 minutes. 35 PCR cycles are then carried out, one cycle consisting of 1 minute at 95° C. for denaturation of the DNA, 2 minutes at 55° C. for hybridization of the amplimers with the single-stranded DNA templates and 2 minutes at 72° C. for elongation of the oligonucleotide primers; the final cycle possesses, in addition, a 7-minute extension of the elongation step in order to terminate the synthesis of incomplete DNA fragments. The concentration of Taq polymerase (Perkin Elmer-Cetus) is 2.5 U for 1 lg of initial RNA. In all cases, the PCR reaction is carried out in buffer comprising 10 Tris pH 8.3, 50 mM KCl, 1.5 mM MgCl$_2$, 0.01% gelatin.

We chose HIV-1 mRNA as a model because it is known to present a complex splicing strategy (Schwartz S., et al. 1990a. J. Virol. 64 (6):2519–2529) linked to the cell type (Robert-Guroff M., et al. 1990. J. Virol. 64 (7):3391–3398) and to the state of differentiation of the cell. The differential splicing leads to three classes of mRNA, unspliced, monospliced and multispliced, which can be identified, respectively, in Northern blotting by three major bands of 9.5, 4.3 and 1.8–2 kb, respectively. However, the HIV mRNAs form a complex family comprising more than 20 mRNAs, and only very sophisticated tools such as the method of protection with ribonucleases or RT-PCR can permit discrimination between several mRNAs in a single class. A further difficulty relates to the secondary structures of high stability occurring in retroviral mRNAs and which could jeopardize the cDNA synthesis reaction.

1/Identification of amplified fragments

Figure 11:
FIG. 11 shows the autoradiographic pictures obtained at the end of the various experiments described in Example 9 (section "Identification of amplified fragments")

The phenotypic typing of HIV mRNAS was carried out using primers specific for the classes described above, chosen from separate exons, respectively 337–335 (Table 1, FIG. 1) for the identification of monospliced mRNAs and 338–335 (Table 1, FIG. 1) for the characterization of multispliced mRNAs. This localization of primers does not permit the amplification of potentially contaminating DNA and of genomic RNA. The same analysis was carried out both for the one-step assays (Table 2, columns K8 and KT) and the two-step assays (Table 2, columns 84 and 74). The amplimers, reverse primers and oligonucleotide probes specific for the various introns and exons are listed in Table 1 and localized in FIG. 1. In FIG. 11, there appears against each band its equivalence in exon junctions, the nomenclature used being that described in FIG. 1. Southern blot analysis (see Example 1) of multispliced mRNAs amplified using the primers 335–338 detected a complex model which may be resolved by means of discriminating probes (FIG. 11, columns K8 and 84). The monospliced mRNAs have not been amplified, as was expected, with the primers 335–338 (FIG. 11, probe 345, columns K8 and 84), since the nucleic acid fragment is too long to be amplified under these PCR conditions. The RNA amplified with the primers 335–338 (FIG. 11, columns K8 and 84) produced a complex model comprising 4 bands which could be interpreted as mRNAs coding for the Nef, Rev, Tat and Vif proteins (Schwartz S., et al. 1990a, J. Virol. 64 (6):2519–2529; Guatelli J. C., et al. 1990, J. Virol. 64 (9):4093–4098; Robert-Guroff M., et al. 1990, J. Virol. 64 (7):3391–3398). The lower band of approximately 231 bp, corresponding to the exons 1-5-7, coding for the Nef protein, was visualized with the probe 344 (exon 5) but not with the upstream probes (343, 455) nor with the Env intron probe (345). The band immediately above, of approximately 247 bp, visualized both with the probe 344 (exon 5) and the probe 343 (exon 4B) but negative with the probes 455 (exon 4) and 345 (intron 4), corresponds to the mRNA coding for Rev following the exon junctions 1-4B-7. The upper bands of approximately 430 to 1295 bp, visualized with all the probes except for that corresponding to the Env intron (345), may correspond to the exons 1-4-7 and 1-2A-7, coding for the Tat and Vif mRNAs, respectively. The additional bands ("a, "b, "c, "d) are difficult to interpret. The bands referred to as "a and "b may be the result of the use of two acceptor sites a4 and a5 (visualized with the probes 344 and 343 but negative with the probe 455), and may represent the mRNAs 1-3-4A-6D-7 (422 bp) and 1-3-4B-6D-7 (436 bp) which may code for an mRNA coding for a protein possessing Rev type activity, as in the case of the Tev protein (Benko D. M., et al. 1990. J. Virol. 64:2505–2518). The band "c of approximately 730 bp is interpreted as an mRNA utilizing the Rev acceptor sites (a4 and a5).

Southern blot analysis (see Example 1) of RNAs amplified with the primers 335–337 (FIG. 11, columns K7 and 74) detected two bands which may be interpreted as mRNAs coding for the Env/Vpu and Tat proteins (Schwartz S., et al. 1990b, J. Virol. 64 (11):5448–5456). The lower band of approximately 530 bp could be the Env/Vpu mRNA, corresponding to the exons 1-5E visualized both with the probes 345 (exon 4) end 344 (exon 5) but negative for the probes present upstream (343 and 455). The band immediately above, of approximately 729 bp, visualized with the probes 345 (intron 4), 455 (exon 4), 343 (exon 4B) and 344 (exon 5), may be interpreted as a 1-4E mRNA coding for the Tat protein. Three bands referred to as "e, "f and "g have still not been explained. The reactivity with the probes 343 and the non-reactivity with the probe 455 would appear to prove that the mRNAs "e and "f use the Rev acceptor sites. In addition, many unexpected bands were observed in the column 74 using the probes 344, 343 and 455 (brackets A, B, C). The typical arrangement of these bands, depending on the signal of the probes and their distribution, enabled them to be identified as resulting from amplification of the multispliced mRNAs (see preceding paragraph, 335–138 amplification). These bands can be identified by the absence of signal with the Env intron probe (345) and by the loss of the typical bands resembling those of Nef and Rev using the probes 343 and 455, respectively. In addition, since their size is approximately 20 bp smaller than that obtained on amplification of the original multipliced mRNAs, these bands do not result from contamination with the primer 338. Immediately upstream of the region of the primer 338 there is the following sequence AAA/ACCCACCTCCCAACCCCGAG (SEQ ID NO: 12) (exon 5/exon 7), which exhibits similarities (underlined) with the reverse Env primer 337 GCAACCACCACTCTATTTTGTG (SEQ ID NO: 13), including 11 potential powerful interactions (A-T, G-C) with a central C-rich core and a weak interaction (G-T) at the 3' terminus. It is thus to be expected that, under non-optimal conditions of reverse transcription, a cDNA will be generated, and that, in the subsequent PCR, this non-specific signal will be amplified considerably. We have, moreover, observed this phenomenon during the study of the different conditions of RT-PCR described below.

2/Quality of the amplification

Figure 12:
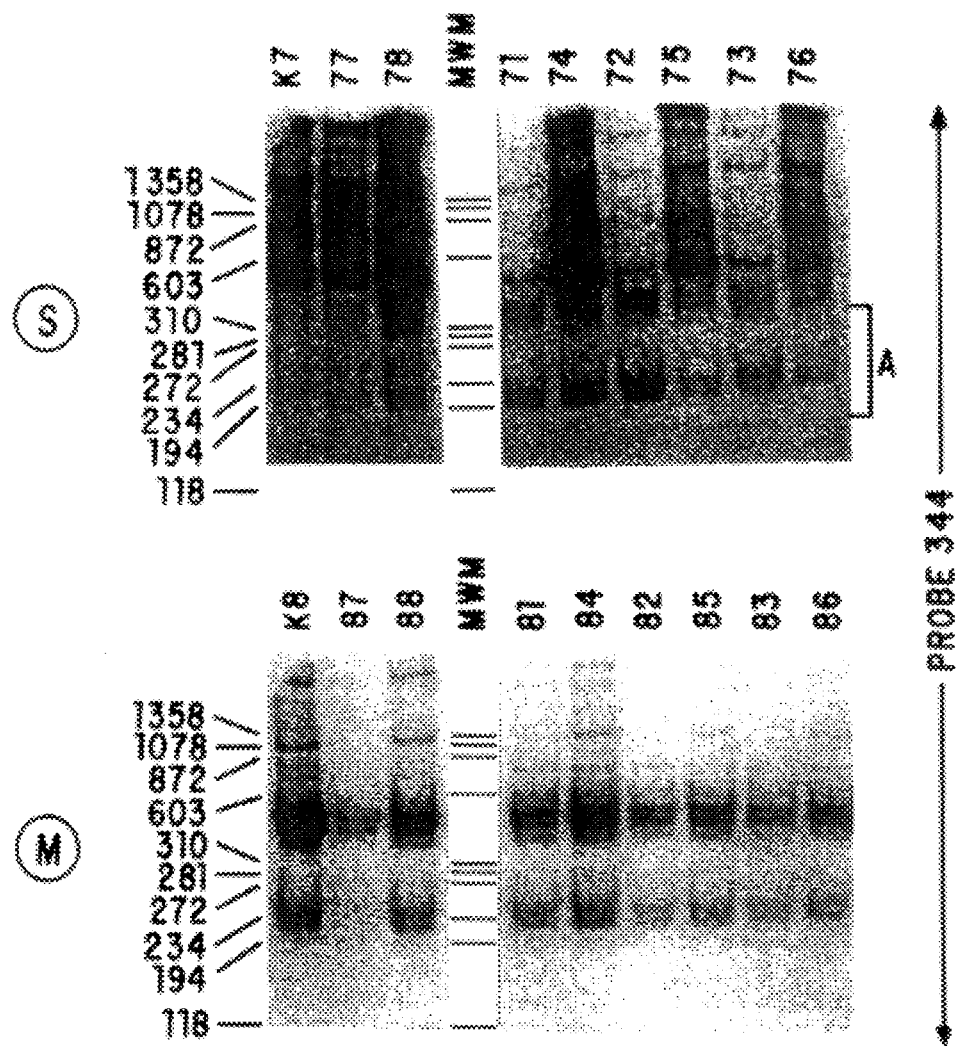
FIG. 12 shows the autoradiographic pictures obtained in the experiments described in Example 9 (section "Quality of the amplification")

RT-PCR includes three steps, successively hybridization of the reverse primer with RNA, cDNA synthesis and PCR amplification. Many protocols describe different conditions for each of these three steps, in particular the hybridization and reverse transcription steps. We have hence tested various ways of carrying out RT-PCR (Table 2), comprising different conditions for hybridization of the reverse primer (Hybridization, step 1) and the synthesis of the cDNA (Reverse transcription, step 2), followed by a standard PCR (PCR, step 3). The data listed in Table 2 relate to the composition of the reaction buffer, the incubation volume, the reaction time and temperature, the concentrations of dNTP, and the concentrations and time of introduction of the amplimers, the Taq polymerase and the reverse transcriptase. The multispliced mRNAs (Table 2: Reg, FIG. 12: M) and the monospliced mRNAS (Table 2: Env, FIG. 12: S), amplified with the primers 335–338 and 335–337, respectively, were analyzed by Southern blotting with the probe 344 (FIG. 12).

2-1/Hybridization

Effect of temperature:

During our experiments, hybridization of the reverse primer showed that, after 10 minutes of denaturation of RNA at 65° C., slow cooling to 42° C. had a deleterious effect on the expected result, both qualitatively and quantitatively. Comparison (FIG. 12S) of the columns 71/74, 72/75 and 73/76 for the amplification of the monospliced mRNAs, detected an increase in unexpected signals (bracket A), of low molecular weight (see above: identification of amplified fragments) corresponding to a drop in the major specific signal (Env/Vpu mRNA 1–5E at 530 bp). Such a drop in the specific signal can also be observed after amplification of multispliced mRNAs (FIG. 12M: 81/84, 82/85, 83/86), though it is smaller and without the appearance of non-specific bands. This suggests that the slow cooling promotes the formation of stable secondary structures that interfere with the RT step. This is more striking in the case of monospliced mRNAs as a result of the high stability of their secondary structure in the region of binding of the Rev protein (Rev Responsive Element: RRE 7325–7531) (Holland S. M., et al. 1990. J. Virol. 64 (12):5966–5975) located in the env intron and described as a very stable secondary structure.

2-2/Reverse transcription

Influences of the hybridization temperature and of the concentration of dNTPs and $MgCl_2$ The efficiency of RT-PCR is improved with a rise in temperature for the RT reaction, as indicated by the increase in the specific signal (FIG. 12S: 74>75>76 and FIG. 12M: 84>85>86). A cDNA synthesis of 45 minutes followed by elongation at 50° C. occasioned qualitative and quantitative disturbances in comparison with direct heating to 50° C. In the buffer PCR*3, with high concentrations of $MgCl_2$ (4.5 mM) and of dNTPs (750 1M), the effect of the temperature is less critical, and best results have been obtained at a uniform temperature (FIG. 12S: 78/74–75 and FIG. 12M: 88/84–85). However, the best (specific signal)/background ratio was obtained with the one-step experiment (FIG. 12M/K7 and FIG. 12S/K8) as a result of the high temperature conditions for the reverse transcription.

EXAMPLE 10

Figure 13:
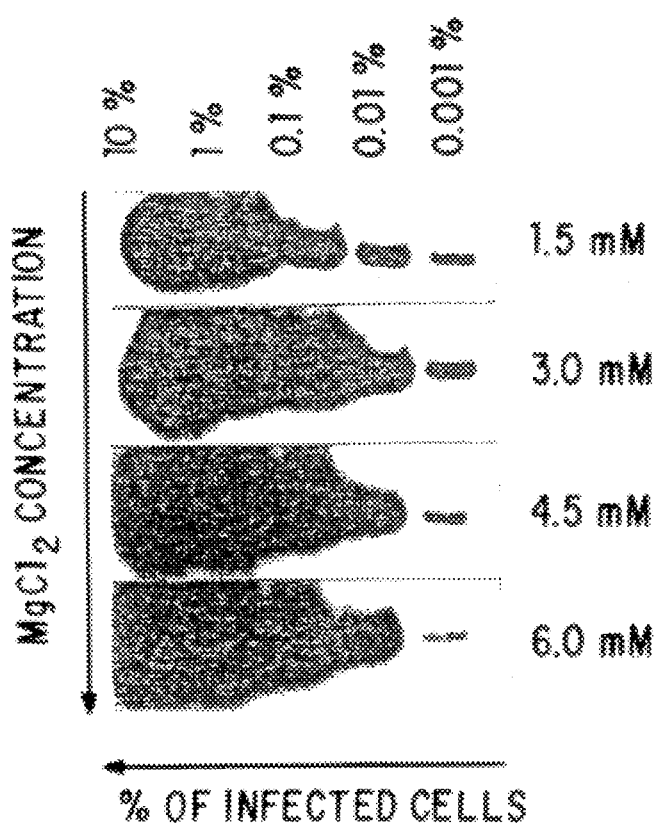
FIGS. 13 and 14 show the autoradiographic pictures obtained in the experiments described in Examples 10 and 11, respectively.

Influence of the $MgCl_2$ concentration in the reaction mixture on the efficiency and sensitivity of the one-step method The experimental conditions used are essentially identical to those described in Example 1. The RNA is extracted from H9 cells infected with the strain HTLV-IIIB, the infected cells representing from 10% to 0.001% of the population treated. The amplification primers are 1082–972 (see Table 1 and FIG. 1). The final concentration of the buffer used is 10 mM Tris pH 8.3, 50 mM KCl, MgCl$_2$ varying from 1.5 mM to 6 mM, 0.01% gelatin. The final concentrations are: 310 nM amplimers, 250 IM dNTPs, 2.5 U Taq polymerase (Perkin Elmer-Cetus), 10 U RT-AMV (Boehringer Mannheim). The amplification protocol, carried out in a thermocycler, consists of an incubation for 10 minutes at 65° C. (denaturation of the RNA and hybridization of the reverse primer, which is itself identical to the 3' amplimer), then 8 minutes at 50° C. (reverse transcription), then 5 minutes at 95° C. (denaturation of the DNA/RNA hybrids and inactivation of the reverse transcriptase), and then, consecutively, 35 PCR cycles are thereafter carried out, one cycle consisting of 1 minute at 95° C. for denaturation of the DNA, 1 minute at 55° C. for hybridization of the amplimers with the single-stranded DNA templates and 1 minute at 72° C. for elongation of the oligonucleotide primers (amplimers); the final cycle possesses, in addition, a 7-minute extension of the elongation step in order to terminate the synthesis of the incomplete DNA fragments. The RT-PCR products are then analyzed by Southern blotting. Southern blot analysis of RNAs amplified with the primers 1082–972 (see Table 1 and FIG. 1) detect in autoradiography the expected band of 340 nucleotides (FIG. 13), visualized with the probe 338 (Table 1, FIG. 1). The MgCl$_2$ concentration does not appreciably influence either the sensitivity or the efficiency of the method. In all cases, a proportion as low as one infected cell out of 100,000 can be detected, and the signal generated by the method shows a correlation with the initial concentration of target RNA.

EXAMPLE 11

Figure 14:
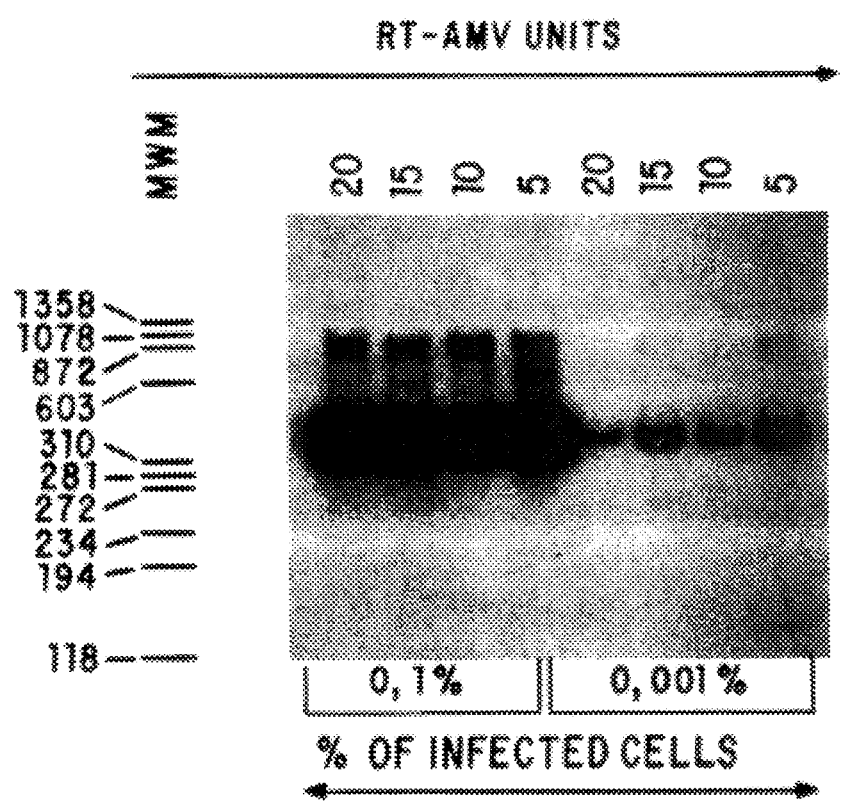

Influence of the RT-AMV/Taq polymerase ratio in the reaction mixture on the efficiency and sensitivity of the one-step method The experimental conditions used are essentially identical to those described in Example 1. The RNA is extracted from H9 cells infected with the strain HTLV-IIIB, the infected cells representing 0.001% or 0.1% of the population treated. The amplification primers are 1082–972 (see Table 1 and FIG. 1). The final concentration of the buffer used is 10 mM Tris pH 8.3, 50 mM KCl, 1.5 mM MgCl$_2$, 0.01% gelatin. The final concentrations are: 310 nM amplimers, 250 IM dNTPs, 2.5 U Taq polymerase (Perkin Elmer-Cetus), 5 U, 10 U, 15 U or 20 U RT-AMV (Boehringer Mannheim). The amplification protocol, carried out in a thermocycler, consists of an incubation for 10 minutes at 65° C. (denaturation of the RNA and hybridization of the reverse primer, which is itself identical to the 3' amplimer), then 8 minutes at 50° C. (reverse transcription), then 5 minutes at 95° C. (denaturation of the DNA/RNA hybrids and inactivation of the reverse transcriptase), and then, consecutively, 35 PCR cycles are thereafter carried out, one cycle consisting of 1 minute at 95° C. for denaturation of the DNA, 1 minute at 55° C. for hybridization of the amplimers with the single-stranded DNA templates and 1 minute at 72° C. for elongation of the oligonucleotide primers (amplimers); the final cycle possesses, in addition, a 7-minute extension of the elongation step in order to terminate the synthesis of the incomplete DNA fragments. The RT-PCR products are then analyzed by Southern blotting. Southern blot analysis of RNAs amplified with the primers 1082–972 (see Table 1 and FIG. 1) detect in autoradiography the expected band of 340 nucleotides (FIG. 14), visualized with the probe 338 (Table 1, FIG. 1). The variations in the RT-AMV/Taq polymerase ratio do not appreciably influence either the sensitivity or the efficiency of the method. In all cases, it is possible to detect a proportion as low as one infected cell out of 100,000, and the signals generated by the method shows a correlation with the initial concentration of target RNA. A substantial drop in the signal is, however, observed with a ratio equal to 8.

We claim:

1. A method for the amplification of RNA in a sample, comprising:

a) obtaining a starting solution by adding to a container the sample, a buffer, a first primer, a second primer, a plurality of nucleotide triphosphates, a sufficient amount of an enzyme system having reverse transcriptase activity and a heat stable enzyme system having DNA polymerase activity, and closing the container, wherein said sufficient amount is an amount which, after the heat treatment of step b) below, will retain sufficient reverse transcriptase activity to permit performance of step c) hereafter;

b) heating the solution obtained in a) to a temperature of 60°–75° C. and maintaining said temperature for a sufficient time to provide denaturation of said RNA without inactivating the enzyme system having reverse transcriptase activity, said time ranging from 1 minute to 15 minutes;

c) bringing the solution obtained in b) to a predetermined temperature of at least 50° C. and maintaining said temperature for sufficient time whereby a first cDNA strand is synthesized and a RNA-cDNA heteroduplex is formed;

d) heating the solution obtained in c) to a predetermined temperature whereby said RNA-cDNA heteroduplex is denatured to form an RNA single strand and a first cDNA single strand;

e) cooling the solution obtained in d) to a predetermined temperature and maintaining said temperature for a sufficient time whereby the second primer hybridizes with the first cDNA strand;

f) bringing the solution obtained in e) to a predetermined temperature and maintaining said temperature for a sufficient time whereby a second cDNA strand is synthesized to form a double-stranded cDNA; and g) denaturing the double-stranded cDNA and subjecting the cDNA strands to a sufficient number of amplification cycles to obtain a desired amount of amplified product.

2. The method as claimed in claim 1, wherein in step b) said solution is heated to at least 65° C.

3. The method as claimed in claim 1, wherein in step c) said predetermined temperature is a temperature which permits the hybridization of the first primer to said RNA without permitting hybridization of the primer to an RNA sequence that is not absolutely complementary.

4. The method as claimed in claim 1, wherein prior to step c) said solution obtained in b) is cooled to a temperature which permits the hybridization of the first primer to an RNA sequence which is not absolutely complementary, said temperature being at least 40° C. and lower than 50° C.

5. The method as claimed in claim 1, wherein in step c) said predetermined temperature is between 50° and 65° C.

6. The method as claimed in claim 5, wherein in step c) said predetermined temperature is between 50° C. and 60° C.

7. The method as claimed in claim 1, wherein in step c) said sufficient time is less than about 15 minutes.

8. The method as claimed in claim 1, wherein said enzyme system having reverse transcriptase activity is selected from the group consisting of avian myoblastosis virus and Moloney murine leukemia virus.

9. The method as claimed in claim 1, wherein the amounts of reverse transcriptase activity and of DNA polymerase activity are such that the ratio of units of reverse transcriptase to units of DNA polymerase is from 2 to 8.

10. The method as claimed in claim 9, wherein said ratio is from 2 to 6.

11. The method as claimed in claim 1, wherein in step d) said predetermined temperature is above 90° C.

12. The method as claimed in claim 1, wherein in step e) said predetermined temperature permits the hybridization of the second primer without permitting hybridization of the second primer to a DNA sequence that is not absolutely complementary.

13. The method as claimed in claim 1, wherein in step e) said predetermined temperature permits the hybridization of the second primer to a DNA sequence which is not absolutely complementary, said temperature being at least 40° C. and lower than 50° C.

14. The method as claimed in claim 1, wherein in step e) said predetermined temperature maintains the hybridization of the second primer.

15. The method as claimed in claim 1, wherein said sample is deposited on or attached to a support.

16. The method as claimed in claim 1, for the amplification of human immunodeficiency virus RNA, wherein the first primer comprises the following sequence:

CCTATCTGTCCCCTCAGCTAC (SEQ ID. NO: 1).

17. The method as claimed in claim 1, for the amplification of human immunodeficiency virus RNA, wherein the second primer comprises the following sequence:

TCTATCAAAGCAACCCAC (SEQ. ID. NO: 2).

18. The method as claimed in claim 15, wherein in step f), said predetermined temperature is at least 50° C.

* * * * *

UNITED STATES PATENT AND TRADEMARK OFFICE
CERTIFICATE OF CORRECTION

PATENT NO. : 5,654,143
DATED : August 5, 1997
INVENTOR(S) : François Mallet, Guy Oriol and Bernard Mandrand It is certified that error appears in the above-identified patent and that said Letters Patent is hereby corrected as shown below:

Column 26,
Line 23, change "step e)" to -- step f) --.

Signed and Sealed this

Third Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 5,654,143
DATED : August 5, 1997
INVENTOR(S) : François Mallet, Guy Oriol and Bernard Mandrand It is certified that error appears in the above-identified patent and that said Letters Patent is hereby corrected as shown below:

Column 26,
Line 37, change "claim 15" to -- claim 14 --.

Signed and Sealed this

Fourteenth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 5,654,143  Page 1 of 1
APPLICATION NO. : 08/412229
DATED : August 5, 1997
INVENTOR(S) : François Mallet, Guy Oriol and Bernard Mandrand It is certified that error appears in the above-identified patent and that said Letters Patent is hereby corrected as shown below:

Col. 2, line 60:

Change "RNA-dependent DNA polymerase activity "
to
--DNA-dependent DNA polymerase activity--.

Signed and Sealed this

Fifteenth Day of August, 2006

JON W. DUDAS
*Director of the United States Patent and Trademark Office*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

CCTATCTGTC CCCTCAGCTA C                         2 1

( 2 ) INFORMATION FOR SEQ ID NO:2:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear (x i) SEQUENCE DESCRIPTION: SEQ ID NO:2:

TCTATCAAAG CAACCCAC 18

(2) INFORMATION FOR SEQ ID NO:3:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (x i) SEQUENCE DESCRIPTION: SEQ ID NO:3:

ATCTCTAGCA GTGGCGCCC 19

(2) INFORMATION FOR SEQ ID NO:4:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (x i) SEQUENCE DESCRIPTION: SEQ ID NO:4:

TTCCTTCGGG CCTGTCGGG 19

(2) INFORMATION FOR SEQ ID NO:5:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (x i) SEQUENCE DESCRIPTION: SEQ ID NO:5:

CACAAAATAG AGTGGTGGTT GC 22

(2) INFORMATION FOR SEQ ID NO:6:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (x i) SEQUENCE DESCRIPTION: SEQ ID NO:6:

TCGTCGCTGT CTCCGCTTCT TC 22

(2) INFORMATION FOR SEQ ID NO:7:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (x i) SEQUENCE DESCRIPTION: SEQ ID NO:7:

CTTCCTGCCA TAGGAGATGC 20

(2) INFORMATION FOR SEQ ID NO:8:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (x i) SEQUENCE DESCRIPTION: SEQ ID NO:8:

```
CTCCATTTCT TGCTCTCCTC TGTC                                              24
```

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:9:

```
CCACACAACT ATTGCTATTA TTA                                               23
```

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:10:

```
AAGAAGCGGA GACAGCGA                                                     18
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

```
AGCAGAAGAC AGTGGCAATG                                                   20
```

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:12:

```
AAAACCCACC TCCCAACCCC GAG                                               23
```

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

```
GCAACCACCA CTCTATTTTG TG                                                22
```